US008968310B2

(12) United States Patent
Twomey et al.

(10) Patent No.: US 8,968,310 B2
(45) Date of Patent: Mar. 3, 2015

(54) ELECTROSURGICAL INSTRUMENT WITH A KNIFE BLADE LOCKOUT MECHANISM

(75) Inventors: John R. Twomey, Longmont, CO (US); Edward M. Chojin, Boulder, CO (US)

(73) Assignee: Covidien LP, Mansfield, MA (US)

(*) Notice: Subject to any disclaimer, the term of this patent is extended or adjusted under 35 U.S.C. 154(b) by 641 days.

(21) Appl. No.: 13/308,104

(22) Filed: Nov. 30, 2011

(65) Prior Publication Data

US 2013/0138102 A1 May 30, 2013

(51) Int. Cl.
*A61B 17/285* (2006.01)
*A61B 18/12* (2006.01)

(52) U.S. Cl.
USPC .......... 606/51; 606/45

(58) Field of Classification Search
CPC .......... A61B 18/1447; A61B 2018/1455; A61B 18/085; A61B 2018/00607; A61B 2018/00994; A61B 2019/481; A61B 18/1445; A61N 2007/025
USPC .......... 606/51, 52, 167, 170, 171
See application file for complete search history.

(56) References Cited

U.S. PATENT DOCUMENTS

| | | | |
|---|---|---|---|
| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| D343,453 | S | 1/1994 | Noda |
| D348,930 | S | 7/1994 | Olson |
| D349,341 | S | 8/1994 | Lichtman et al. |
| D354,564 | S | 1/1995 | Medema |
| D358,887 | S | 5/1995 | Feinberg |
| D384,413 | S | 9/1997 | Zlock et al. |
| H1745 | H | 8/1998 | Paraschac |
| D402,028 | S | 12/1998 | Grimm et al. |
| D408,018 | S | 4/1999 | McNaughton |
| D416,089 | S | 11/1999 | Barton et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Paula J Stice
*Assistant Examiner* — Erin Piateski

(57) ABSTRACT

An electrosurgical forceps is provided with a shaft that extends from a housing of the electrosurgical forceps. An end effector assembly operably coupled to the shaft includes a pair of first and second jaw members. One or both of the first and second jaw members is movable from an open configuration, to a clamping configuration. A knife blade assembly includes a knife blade translatable within the first and second jaw members. A knife blade lockout mechanism is in operative communication with the knife blade assembly and includes an elongated cam slot with a cam pin translatable therein from a distal end of the elongated cam slot corresponding to the knife blade lockout mechanism engaged with the knife blade assembly, to a proximal position corresponding to the knife blade lockout mechanism disengaged from the knife blade assembly.

20 Claims, 13 Drawing Sheets

(56) References Cited

U.S. PATENT DOCUMENTS

| | | | | |
|---|---|---|---|---|
| D424,694 | S | 5/2000 | Tetzlaff et al. | |
| D425,201 | S | 5/2000 | Tetzlaff et al. | |
| H1904 | H | 10/2000 | Yates et al. | |
| D449,886 | S | 10/2001 | Tetzlaff et al. | |
| D453,923 | S | 2/2002 | Olson | |
| D454,951 | S | 3/2002 | Bon | |
| D457,958 | S | 5/2002 | Dycus et al. | |
| D457,959 | S | 5/2002 | Tetzlaff et al. | |
| H2037 | H | 7/2002 | Yates et al. | |
| D465,281 | S | 11/2002 | Lang | |
| D466,209 | S | 11/2002 | Bon | |
| D493,888 | S | 8/2004 | Reschke | |
| D496,997 | S | 10/2004 | Dycus et al. | |
| D499,181 | S | 11/2004 | Dycus et al. | |
| D502,994 | S | 3/2005 | Blake, III | |
| D509,297 | S | 9/2005 | Wells | |
| 7,001,382 | B2 | 2/2006 | Gallo et al. | |
| D525,361 | S | 7/2006 | Hushka | |
| D531,311 | S | 10/2006 | Guerra et al. | |
| D533,274 | S | 12/2006 | Visconti et al. | |
| D533,942 | S | 12/2006 | Kerr et al. | |
| D535,027 | S | 1/2007 | James et al. | |
| D538,932 | S | 3/2007 | Malik | |
| D541,418 | S | 4/2007 | Schechter et al. | |
| D541,611 | S | 5/2007 | Aglassinger | |
| D541,938 | S | 5/2007 | Kerr et al | |
| D545,432 | S | 6/2007 | Watanabe | |
| D547,154 | S | 7/2007 | Lee | |
| D564,662 | S | 3/2008 | Moses et al. | |
| D567,943 | S | 4/2008 | Moses et al. | |
| D575,395 | S | 8/2008 | Hushka | |
| D575,401 | S | 8/2008 | Hixson et al. | |
| D582,038 | S | 12/2008 | Swoyer et al. | |
| D617,900 | S | 6/2010 | Kingsley et al. | |
| D617,901 | S | 6/2010 | Unger et al. | |
| D617,902 | S | 6/2010 | Twomey et al. | |
| D617,903 | S | 6/2010 | Unger et al. | |
| D618,798 | S | 6/2010 | Olson et al. | |
| D621,503 | S | 8/2010 | Otten et al. | |
| D627,462 | S | 11/2010 | Kingsley | |
| D628,289 | S | 11/2010 | Romero | |
| D628,290 | S | 11/2010 | Romero | |
| D630,324 | S | 1/2011 | Reschke | |
| 7,922,718 | B2 | 4/2011 | Moses et al. | |
| 7,942,303 | B2 | 5/2011 | Shah | |
| 7,959,051 | B2 | 6/2011 | Smith et al. | |
| D649,249 | S | 11/2011 | Guerra | |
| D649,643 | S | 11/2011 | Allen, IV et al. | |
| 2004/0087943 | A1* | 5/2004 | Dycus et al. | 606/51 |
| 2006/0030870 | A1* | 2/2006 | Staudner | 606/167 |
| 2006/0271042 | A1* | 11/2006 | Latterell et al. | 606/51 |
| 2007/0088375 | A1* | 4/2007 | Beane et al. | 606/167 |
| 2007/0260242 | A1* | 11/2007 | Dycus et al. | 606/51 |
| 2007/0260275 | A1* | 11/2007 | Ahlberg et al. | 606/185 |
| 2009/0182327 | A1 | 7/2009 | Unger | |
| 2010/0114137 | A1* | 5/2010 | Vidal et al. | 606/167 |
| 2010/0179540 | A1* | 7/2010 | Marczyk et al. | 606/41 |
| 2010/0179545 | A1* | 7/2010 | Twomey et al. | 606/51 |
| 2010/0204697 | A1* | 8/2010 | Dumbauld et al. | 606/51 |
| 2010/0274244 | A1* | 10/2010 | Heard | 606/45 |
| 2011/0054469 | A1 | 3/2011 | Kappus et al. | |
| 2011/0184405 | A1* | 7/2011 | Mueller | 606/41 |
| 2011/0251612 | A1* | 10/2011 | Faller et al. | 606/52 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.

(56) References Cited

OTHER PUBLICATIONS

U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.

(56) References Cited

OTHER PUBLICATIONS

Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/USO4/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

ELECTROSURGICAL INSTRUMENT WITH A KNIFE BLADE LOCKOUT MECHANISM

BACKGROUND

1. Technical Field

The present disclosure relates to an electrosurgical instrument and, more particularly, to an electrosurgical instrument including jaw members and a knife blade lockout mechanism that is configured to prevent unintentional deployment of a knife blade when the jaw members are in a spaced-apart configuration.

2. Description of Related Art

Electrosurgical forceps are well known in the medical arts. For example, an electrosurgical endoscopic forceps is utilized in surgical procedures, e.g., laparoscopic surgical procedure, where access to tissue is accomplished through a cannula or other suitable device positioned in an opening on a patient. The endoscopic forceps, typically, includes a housing; a handle assembly including a movable handle; a drive assembly; a shaft; a cutting mechanism such as, for example, a knife blade assembly; and an end effector assembly attached to a distal end of the shaft. The end effector includes jaw members that operably communicate with the drive assembly to manipulate tissue, e.g., grasp and seal tissue. Typically, the endoscopic forceps utilizes both mechanical clamping action and electrical energy to effect hemostasis by heating the tissue and blood vessels to coagulate, cauterize, seal, cut, desiccate, and/or fulgurate tissue. Typically, subsequent to effecting hemostasis, a knife blade of the knife blade assembly is deployed to sever the effected tissue.

Conventional endoscopic forceps, typically, utilize a safety blade lockout mechanism that prevents the blade from being unintentionally deployed. In particular, an endoscopic forceps may be configured to utilize a direct interaction between a lever and a trigger (or via another linkage in the lever mechanism) on the handle assembly to prevent the knife blade from being unintentionally deployed. That is, the knife blade is prevented from moving or translating into a knife slot on one or both of the jaw members. Under certain surgical scenarios, however, such as, for example, when the lever is in a "latched" configuration (i.e., the knife blade is operable to sever tissue) and a thick bundle of tissue is positioned between the jaw members, there exists a possibility of the knife blade deploying and wandering or drifting out of the knife slot(s) on the jaw member(s) and becoming trapped between the jaw members when they are moved to the clamping configuration. This condition is commonly referred to in the art as "blade trap." As can be appreciated, "blade trap" may cause a cutting edge of the knife blade to ineffectively sever electrosurgically treated tissue, i.e., the knife blade may not fully or "swiftly" sever the electrosurgically treated tissue.

SUMMARY

Aspects of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user. As used herein, electrosurgical energy refers to, without limitation, electrical energy, ultrasonic energy, thermal energy and/or mechanical energy used in combination with one of the aforementioned other energies.

According to an aspect of the invention disclosure, an electrosurgical forceps is provided. The electrosurgical forceps includes a shaft that extends from a housing of the electrosurgical forceps. A longitudinal axis is defined through the shaft. An end effector assembly operably coupled to a distal end of the shaft includes a pair of first and second jaw members. One or both of the first and second jaw members is movable from an open configuration, to a clamping configuration. A knife blade assembly includes a knife blade that is translatable within the first and second jaw members when the first and second jaw members are in the clamping configuration to sever tissue. A knife blade lockout mechanism is in operative communication with the knife blade assembly. The knife blade lockout mechanism includes an elongated cam slot with a cam pin translatable therein. The cam pin is translatable within the elongated cam slot from a distal end of the elongated cam slot corresponding to the first and second jaw members being in the open configuration and the knife blade lockout mechanism engaged with the knife blade assembly, to a proximal position corresponding to the first and second jaw members being in the clamping configuration and the knife blade lockout mechanism disengaged from the knife blade assembly.

In accordance with the instant disclosure, when the knife blade lockout mechanism is engaged with the knife blade assembly, the knife blade assembly is prevented from translating within the first and second jaw members, and when knife blade lockout mechanism is disengaged from the knife blade assembly the knife blade is capable of translating within the first and second jaw members. In certain instances, when the knife blade lockout mechanism is engaged with the knife blade assembly, the knife blade lockout mechanism could be used to limit the travel of the knife blade assembly. In this instance, the knife blade assembly could deploy partially, but not beyond a "safe" distance where the knife blade assembly is at risk of becoming trapped between the first and second jaw members. As can be appreciated, this may prevent a surgeon from becoming frustrated (or confused) that the knife blade assembly cannot be deployed and would maintain partial functionality of the knife blade assembly even on thick tissue.

In accordance with the instant disclosure, the knife blade lockout mechanism may include a generally rectangular configuration having open leading and trailing ends. In certain instances, the open leading end may be configured to selectively engage a notched portion of the knife blade assembly. Moreover, a protrusion may be disposed adjacent the open trailing end of the knife blade lockout mechanism and may be configured to selectively engage a notched portion of the knife blade assembly.

In certain instances, the knife blade lockout mechanism may be operably positioned between the first and second jaw members. In this particular instance, the first and second jaw members may be pivotably coupled to one another via a pivot pin extending through the knife lockout mechanism and the shaft. Moreover, the earn pin disposed within the elongated cam slot may be disposed within respective cam slots of the first and second jaw members and operably coupled to a drive tube of the electrosurgical forceps to move the first and second jaw members from the open position to the clamping position. In this instance, the knife blade lockout mechanism may be pivotable about the pivot pin to provide selective engagement between the knife blade lockout mechanism and the knife blade assembly.

In certain instances, the knife blade lockout mechanism may be positioned proximal to the first and second jaw members. In this particular instance, the first and second jaw members may be pivotably coupled to one another via a pivot pin extending through the shaft. Moreover, the cam pin disposed within the elongated cam slot of the knife blade lockout mechanism may be disposed within respective cam slots of the first and second jaw members. The cam pin may be operably coupled to a drive tube of the electrosurgical forceps to move the first and second jaw members from the open position to the clamping position.

In certain instances, the knife blade lockout mechanism may be positioned proximal to the first and second jaw members. In this particular instance, the first and second jaw members may be pivotably coupled to one another via a first pivot pin extending through the shaft. A second pivot pin extending through the knife blade lockout mechanism is positioned within a pair of slots defined through the drive tube such that the knife blade lockout mechanism pivots about the second pivot pin when the drive tube is actuated. Distal ends of the pair of slots defined in the drive tube may function as a hard stop for the first and second jaw members to provide a predetermined gap distance between the first and second jaw members when the first and second jaw members are in the clamping position. A knife blade assembly return spring that is configured to return the knife blade assembly to an initial retracted position may be operably coupled to the knife blade assembly.

According to another aspect of the instant disclosure, an electrosurgical forceps is provided. The electrosurgical forceps includes shaft that extends from a housing of the electrosurgical forceps. A longitudinal axis is defined through the shaft. An end effector assembly operably coupled to a distal end of the shaft includes a pair of first and second jaw members. One or both of the first and second jaw members is movable from an open configuration, to a clamping configuration. A knife blade assembly includes a knife blade that is translatable within the first and second jaw members when the first and second jaw members are in the clamping configuration to sever tissue. A knife blade lockout mechanism is selectively engageable with the knife blade assembly to lock the knife blade in an initial retracted position. The knife blade lockout mechanism is configured to allow passage of the knife blade assembly therethrough. The knife blade lockout mechanism includes an elongated cam slot with a cam pin translatable therein. The cam pin is translatable within the elongated cam slot from a distal end of the elongated cam slot corresponding to the first and second jaw members being in the open configuration and the knife blade lockout mechanism engaged with the knife blade assembly, to a proximal position corresponding to the first and second jaw members being in the clamping configuration and the knife blade lockout mechanism disengaged from the knife blade assembly.

In accordance with the instance application, the knife blade lockout mechanism may include a generally rectangular configuration having open leading and trailing ends, wherein at least one of the open leading and trailing ends is configured to selectively engage a notched portion of the knife blade assembly. In certain instances, the knife blade lockout mechanism may be operably positioned between the first and second jaw members.

In certain instances, the knife blade lockout mechanism may be operably positioned between the first and second jaw members. In this particular instance, the first and second jaw members may be pivotably coupled to one another via a pivot pin extending through the knife lockout mechanism and the shaft. Moreover, the cam pin disposed within the elongated cam slot may be disposed within respective cam slots of the first and second jaw members and operably coupled to a drive tube of the electrosurgical forceps to move the first and second jaw members from the open position to the clamping position. In this instance, the knife blade lockout mechanism may be pivotable about the pivot pin to provide selective engagement between the knife blade lockout mechanism and the knife blade assembly.

In certain instances, the knife blade lockout mechanism may be positioned proximal to the first and second jaw members. In this particular instance, the first and second jaw members may be pivotably coupled to one another via a pivot pin extending through the shaft. Moreover, the cam pin disposed within the elongated cam slot of the knife blade lockout mechanism may be disposed within respective cam slots of the first and second jaw members. The cam pin may be operably coupled to a drive tube of the electrosurgical forceps to move the first and second jaw members from the open position to the clamping position.

In certain instances, the knife blade lockout mechanism may be positioned proximal to the first and second jaw members and the first and second jaw members may be pivotably coupled to one another via a first pivot pin extending through the shaft. In this particular instance, a second pivot pin extending through the knife blade lockout mechanism is positioned within a pair of slots defined through the drive tube such that the knife blade lockout mechanism pivots about the second pivot pin when the drive tube is actuated. Distal ends of the pair of slots defined in the drive tube may function as a hard stop for the first and second jaw members to provide a predetermined gap distance between the first and second jaw members when the first and second jaw members are in the clamping position. A knife blade assembly return spring that is configured to return the knife blade assembly to an initial retracted position may be operably coupled to the knife blade assembly.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
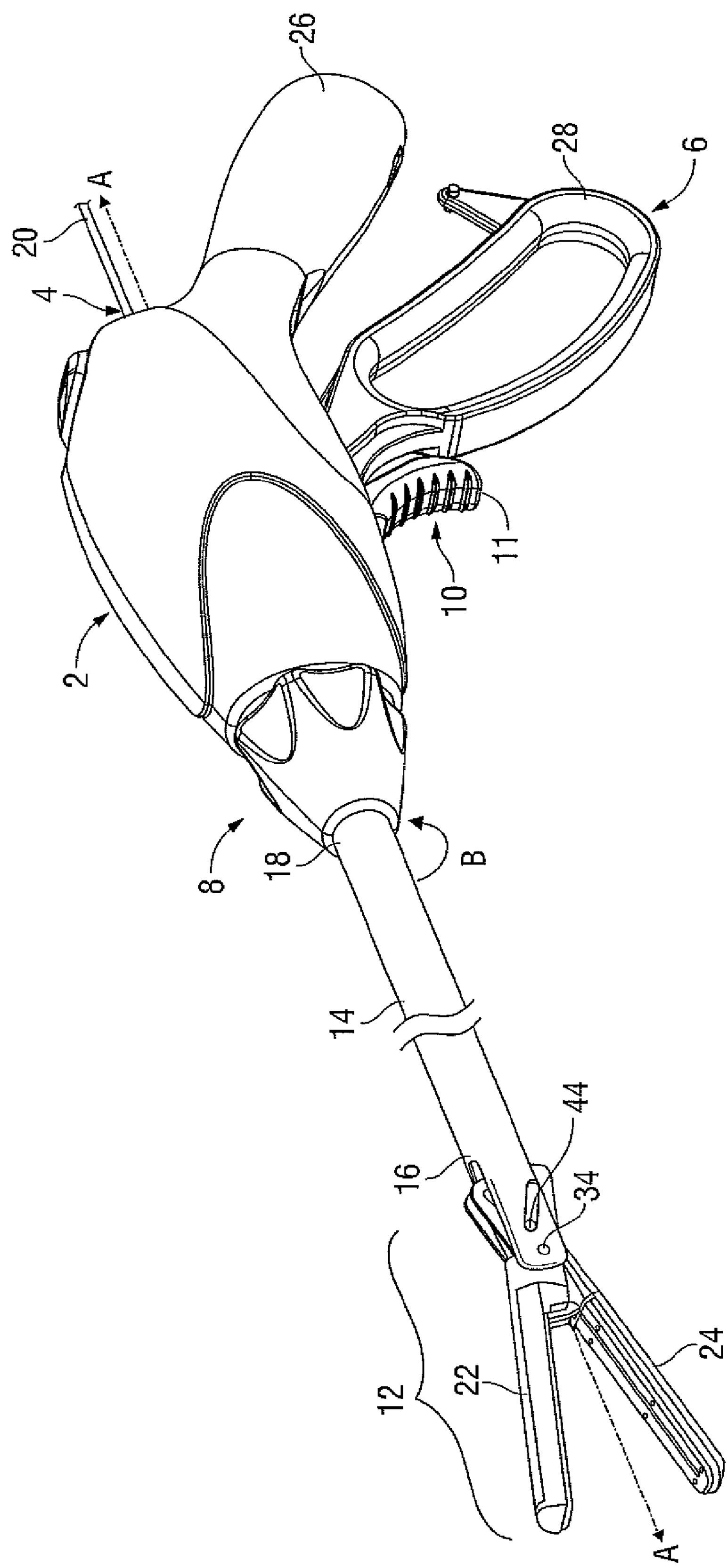
FIG. 1 is a perspective view of an endoscopic electrosurgical forceps according to an embodiment of the present disclosure.

Turning now to FIG. 1, an electrosurgical endoscopic forceps 2 configured for use with a knife blade lockout mechanism 40 (mechanism 40, see FIG. 3) is illustrated. Forceps 2 is provided having a longitudinal axis "A-A" defined therethrough, a housing 4, a handle assembly 6, a rotating assembly 8, a trigger assembly 10 and an end effector assembly 12. Forceps 2 further includes a shaft 14 having a distal end 16 configured to mechanically engage end effector assembly 12 and a proximal end 18 that mechanically engages housing 4. Forceps 2 also includes electrosurgical cable 20 that connects forceps 2 to a generator (not shown) or other suitable power source, although forceps 2 may alternatively be configured as a battery powered instrument. Cable 20 includes a wire (or wires) (not explicitly shown) extending therethrough that has sufficient length to extend through shaft 14 in order to provide electrosurgical energy, e.g., electrical energy, to one or both of a pair of jaw members 22 and 24 of end effector assembly 12. In certain embodiments, the jaw members 22 and 24 may be configured to treat tissue with ultrasonic energy, thermal energy, mechanical energy or combinations thereof. Additionally, while the mechanism 40 is described herein configured for use with an endoscopic forceps 2, it is within the purview of the present disclosure to configure the mechanism 40 for use with open style forceps.

Rotating assembly 8 is rotatable in either direction about longitudinal axis "A-A" to rotate end effector 12 about longitudinal axis "A-A," FIG. 1.

Housing 4 houses the internal working components of forceps 2, such as a drive assembly (not explicitly shown), working components of the handle assembly 6, electrical raceways associated with the cable 20, and other working components therein.

Figure 2:
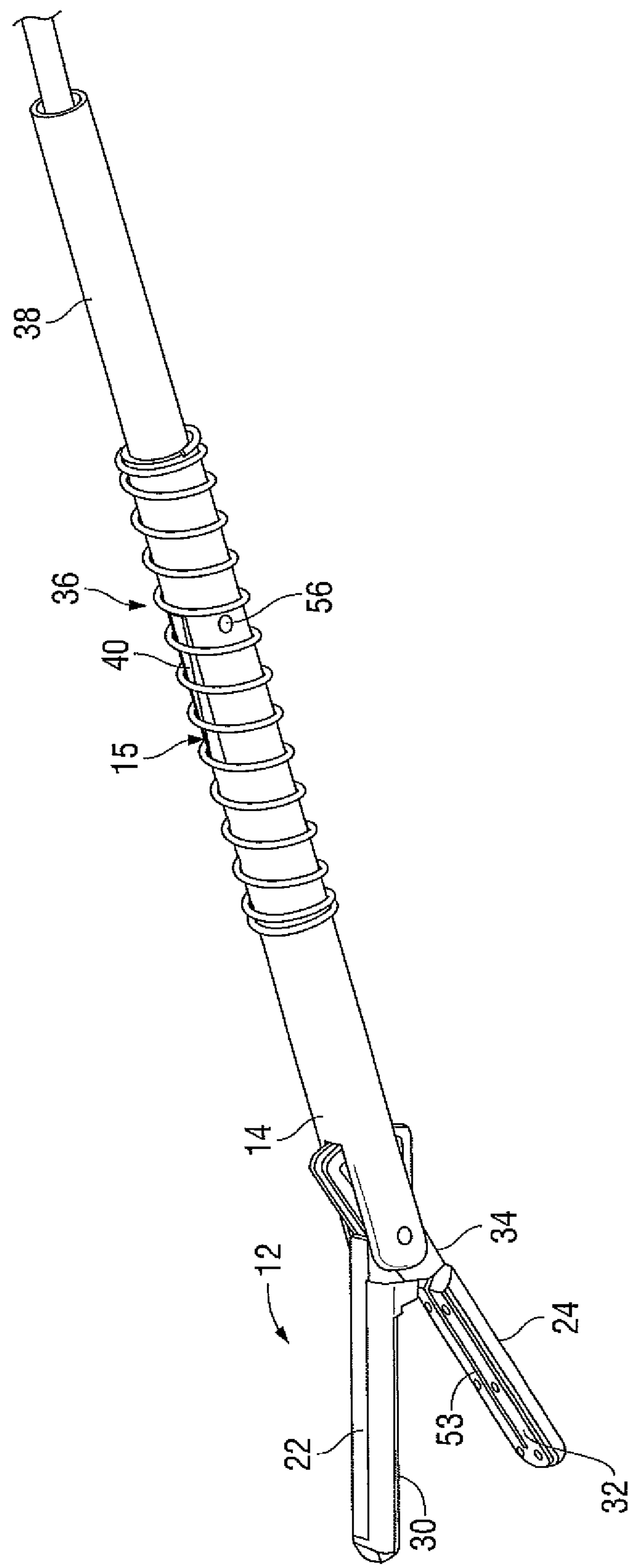
FIG. 2 is a partial, perspective view of the endoscopic electrosurgical forceps with a housing thereof removed to illustrate a front-end assembly including a shaft, a drive tube, knife blade lockout mechanism and a blade return spring.
Figure 3:
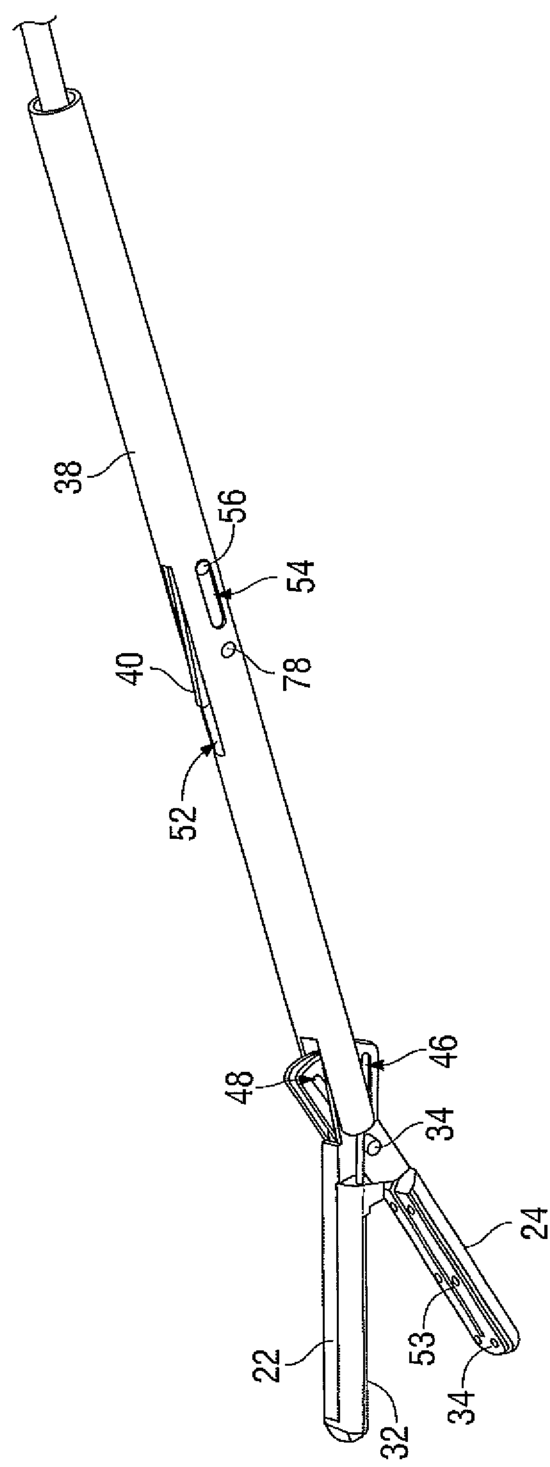
FIG. 3 is a partial, perspective view of the front-end assembly depicted in FIG. 2 with the shaft removed to illustrate the drive tube and knife blade lockout mechanism.
Figure 8:
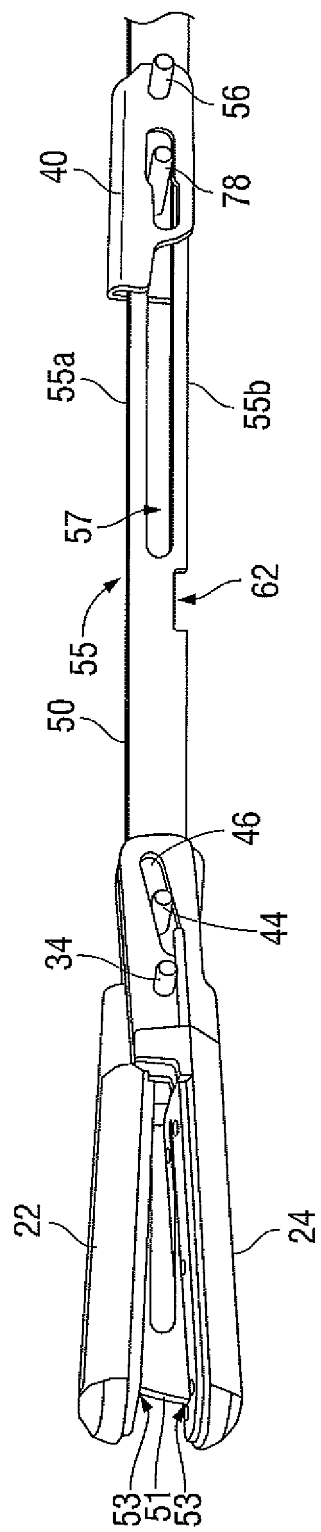
FIG. 8 is a partial, perspective view of the knife blade assembly and blade lockout mechanism in the disengaged configuration with a knife blade member of the knife blade assembly in a deployed position.

With continued reference to FIG. 1, handle assembly 6 includes a fixed handle 26 and a moveable handle 28. Fixed handle 26 is integrally associated with housing 4 and handle 28 is moveable relative to fixed handle 26. Moveable handle 28 of handle assembly 6 is ultimately connected to the drive assembly such that, together, handle 28 and drive assembly mechanically cooperate to impart movement of jaw members 22 and 24 between a spaced-apart position and a clamping position to grasp tissue disposed between sealing surfaces 30 and 32 of jaw members 22, 24, respectively. As shown in FIG. 1, moveable handle 28 is initially spaced-apart from fixed handle 26 and, correspondingly, jaw members 22, 24 are in the spaced-apart position (FIGS. 1-3). Moveable handle 28 is depressible from this initial position to a depressed position (not explicitly shown) corresponding to the approximated position of jaw members 22, 24 (FIG. 8 illustrates the jaw members 22, 24 in a partially approximated position.

Figure 5:
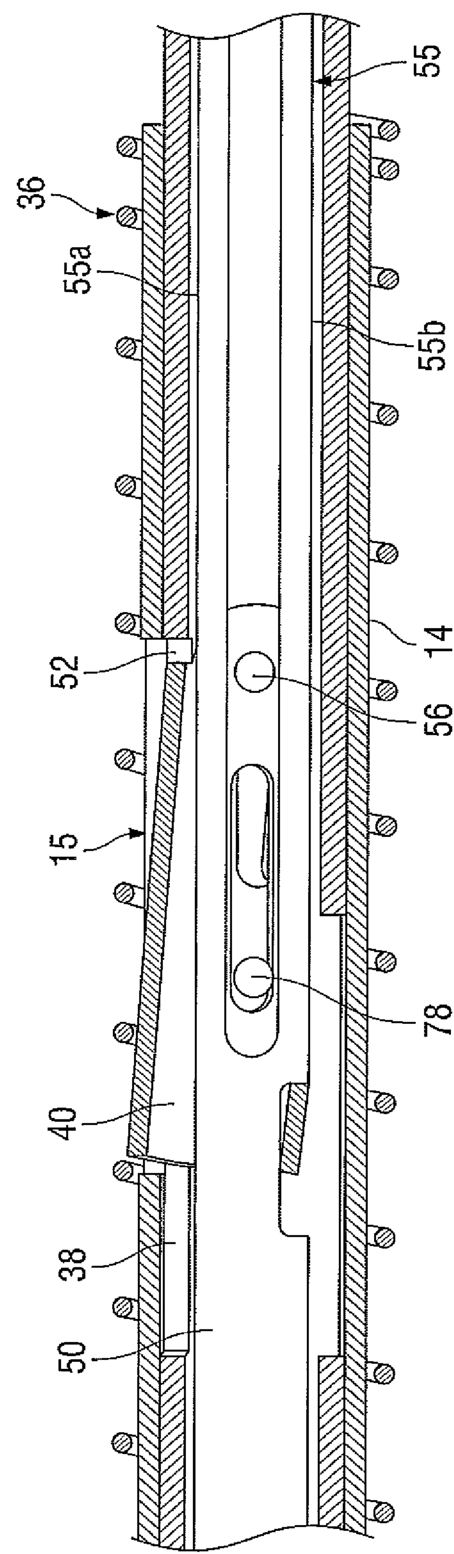
FIG. 5 is a partial, cross-sectional view of the shaft, drive tube, knife blade lockout mechanism, knife blade assembly and blade return spring with the knife blade lockout mechanism in the engaged configuration.
Figure 6:
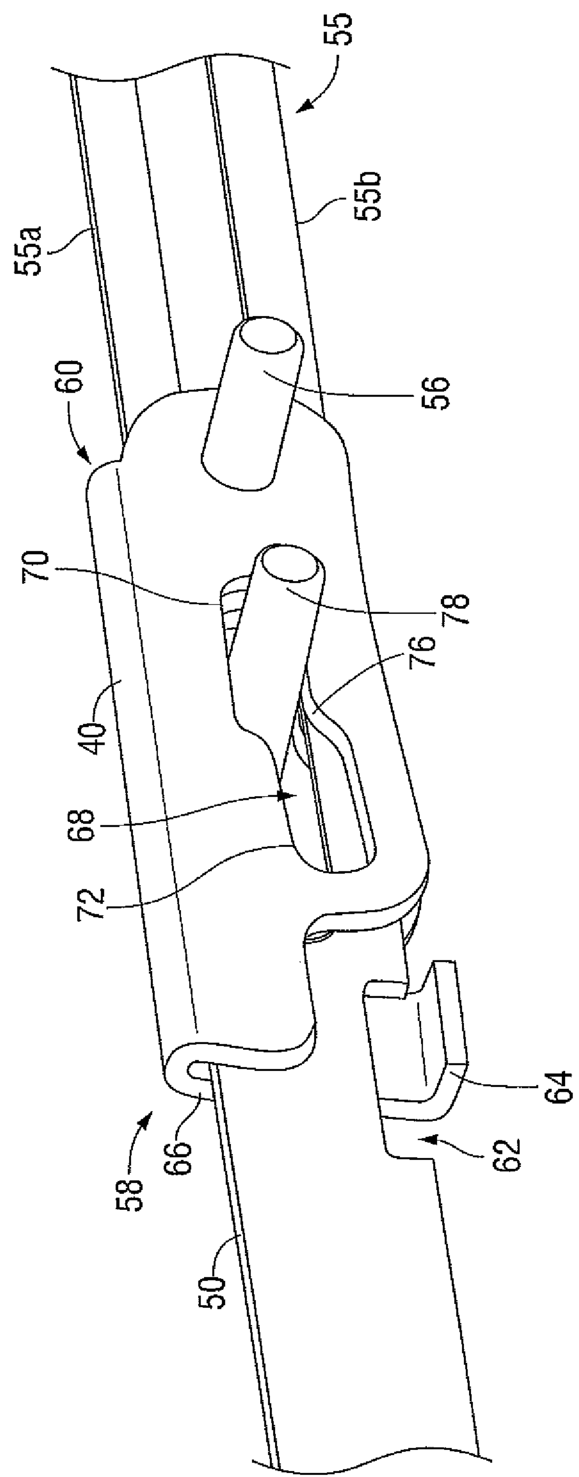
FIG. 6 is partial, perspective view of the knife blade assembly including the knife blade lockout mechanism operably coupled thereto and in a disengaged configuration.
Figure 7:
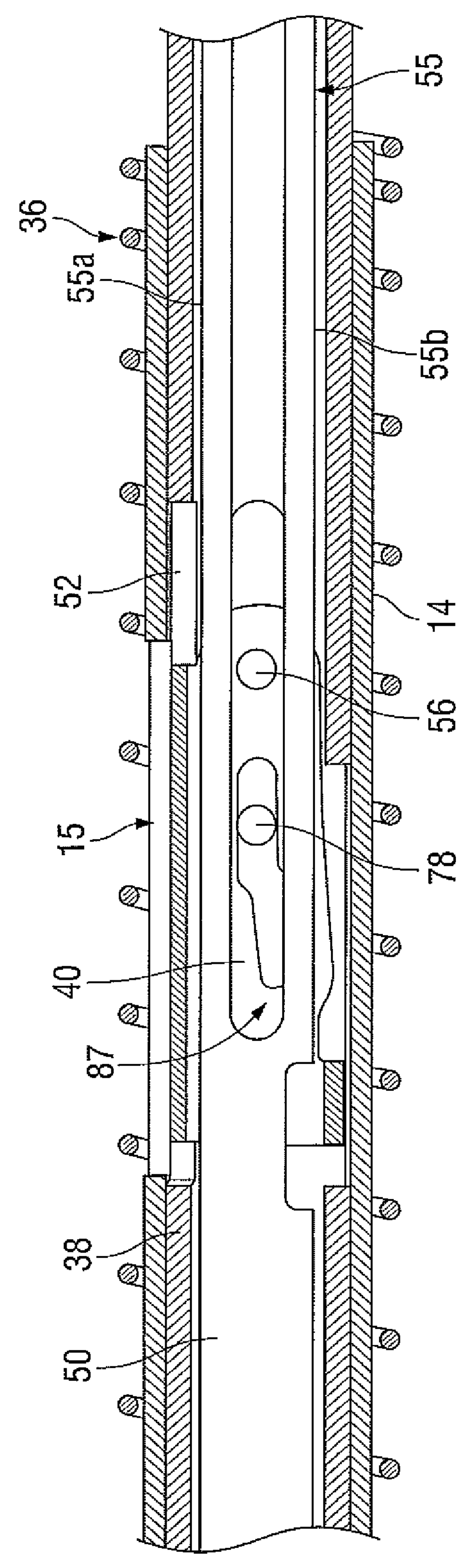
FIG. 7 is a partial, cross-sectional view of the shaft, drive tube, knife blade lockout mechanism, knife blade assembly and blade return spring with the knife blade lockout mechanism in the disengaged configuration.

With reference again to FIG. 1 and with reference to FIGS. 2, 5 and 7, shaft 14 is illustrated. For illustrative purposes in FIG. 2, the housing 4 and rotating assembly 8 are removed to better illustrate the shaft 14 and operative components associated therewith. Shaft 14 includes a generally elongated configuration and is configured to support the jaw members 22, 24 at a distal end 16 thereof via a pivot pin 34 (FIGS. 1-3 and 8). Shaft 14 is also configured to provide passage of a drive tube 38 (FIGS. 2-3 and 5-7) therethrough to move the jaw members 22, 24 from the spaced-apart position to the clamping position.

Shaft 14 includes a generally elongated slot 15 of suitable configuration (FIGS. 2, 5 and 7) to allow the mechanism 40 (or top portion thereof) to pivot therethrough when the mechanism 40 is moved into engagement with a knife blade assembly 50 (see FIGS. 2 and 5), described in greater detail below.

Drive tube 38 (FIGS. 2-3, 5 and 7) is operably coupled to the drive assembly to effect movement of the jaw members 22, 24 and to move the mechanism 40 into and out of engagement with knife blade assembly 50, described in greater detail below. Toward these ends, drive tube 38 includes a tubular configuration and couples to the movable handle 28 via one or more components including, but not limited to, gears, links, sleeves, etc. (not shown). Drive tube 38 is configured to translate through the shaft 14 when the movable handle 28 is moved from its initial position to the depressed position. Drive tube 38 couples the jaw members 22, 24 via a cam pin 44 (FIG. 8). In particular, cam pin 44 is positioned within respective cam slots 46 and 48 on the jaw members 22, 24 (see FIG. 3 in combination with FIG. 8).

Alternately, the jaw members 22, 24 may be opened and closed via a linkage system (not shown) or the like. In this instance, the linkage system can be housed within the housing 4 and coupled to the movable handle 28 by one or more suitable coupling methods to effect movement of one or both of the jaw members 22, 24.

Drive tube 38 includes a first slot 52 that is in vertical registration with the slot 15 on the shaft 14 (FIGS. 5 and 7) to allow the mechanism 40 (or top portion thereof) to pivot therethrough when the mechanism 40 is moved into engagement with a knife blade assembly 50 (see FIGS. 2-3 and 5), described in greater detail below. In certain instance, the cam slot 52 may be configured to allow the mechanism 40 to be assembled into the drive tube 38. As can be appreciated, this can reduce the overall manufacturing costs of the forceps 2.

Drive tube 38 includes a pair of second slots 54 (FIG. 3 illustrates one (1) of the two (2) slots 54) of suitable configuration that are configured to house a pivot pin 56 (FIG. 3) therein such that the mechanism 40 is pivotable thereabout when the drive tube 38 is translated in either the proximal or distal direction. In the embodiment illustrated in FIGS. 1-8, the second slots 54 are oriented approximately 90° from the slots 52 and 15 on the respective drive tube 38 and shaft 14, and 180° from one another; this facilitates pivoting of the mechanism 40 about the pivot pin 56.

In certain instances, a distal end of the second slots 54 may be configured to function as a hard stop for the jaw members 22, 24 to provide a predetermined gap distance between the jaw members 22, 24 when the jaw members 22, 24 are in the clamping position.

Figure 4:
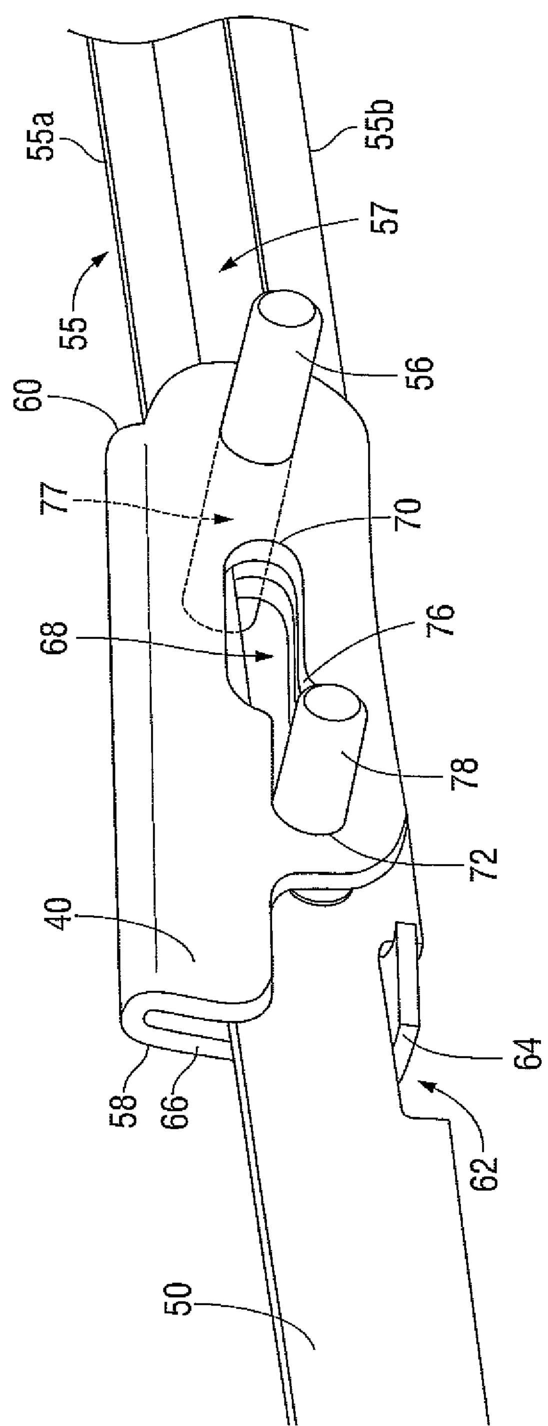
FIG. 4 is partial, perspective view of a knife blade assembly including the knife blade lockout mechanism operably coupled thereto and in an engaged configuration.

Continuing with reference to FIGS. 2-8, mechanism 40 is in operative communication with the knife blade assembly 50. Mechanism 40 includes a generally rectangular configuration that compliments the shape of the knife blade assembly 50 (FIGS. 4-8). Mechanism 40 includes open leading and trailing ends 58 and 60, respectively. Open leading end 58 is configured to selectively engage a notched portion 62 of the knife, blade assembly 50 (FIG. 4). To facilitate engagement of the open leading end 58 with the notched portion 62 of the knife blade assembly 50, the open leading end 58 includes a finger portion 64 that extends laterally across the longitudinal axis "A-A" from a left sidewall 66 of the mechanism 40 thus forming a generally "L" shape (FIGS. 4 and 6). In certain embodiments, such as the embodiments described with respect to FIGS. 9-17, open leading end 58 may include, for example, one or more other configurations and/or structures to facilitate engagement of the open leading end 58 with the notched portion 62; a detailed description of these embodiments is discussed below.

Mechanism 40 includes an elongated cam slot 68 having proximal and distal ends, 70 and 72, respectively (FIGS. 4 and 6). A ramp portion 76 (as best seen in FIG. 6) is disposed between the respective proximal and distal ends 70 and 72 and is configured to pivot the mechanism 40 about the pivot pin 56 when a cam pin 78 that is housed within the cam slot 68 comes in contact with the ramp portion 76.

An aperture 77 (shown in phantom in FIG. 4) of suitable proportion is provided on the mechanism 40 and is configured to receive the pivot pin 56 therethrough such that the mechanism 40 is free to pivot thereabout when the cam pin 78 contacts the ramp portion 76.

Cam pin 78 (FIGS. 3-8) is operably coupled to the drive tube 38 via one or more suitable coupling methods. In the illustrated embodiment, cam pin 78 is ultrasonically welded to the drive tube 38.

Proximal translation of the drive tube 38 translates the cam pin 78 within the elongated slot 68 from the distal end 72 (corresponding to the jaw members 22, 24 being in the open configuration and the mechanism 40 engaged with the knife blade assembly 50, see FIGS. 3 and 4) towards the proximal end 70 (corresponding to the jaw members 22, 24 being in the clamping configuration and the mechanism 40 disengaged from the knife blade assembly, see FIGS. 6 and 8). Prior to the cam pin 78 reaching the proximal end 72, the cam pin 78 contacts the ramp portion 76, which, in turn, causes the mechanism 40 to pivot about the pivot pin 56, which, in turn, causes the finger portion 64 to disengage from the notched portion 62 of the knife blade assembly 50. With the finger portion 64 disengaged from the notched portion 62, the knife blade 51 of the knife blade assembly 50 is free to translate within a pair of knife blade channels 53 disposed on the jaw members 22, 24 of the end effector 12 (FIGS. 2-3 and 8).

With reference again to FIGS. 2-3 and 8, end effector assembly 12 is designed as a bilateral assembly, i.e., where both jaw member 22 and jaw member 24 are moveable about pivot pin 34 relative to one another and to shaft 14. However, end effector assembly 12 may alternatively be configured as a unilateral assembly, i.e., where jaw member 24 is fixed relative to shaft 14 and jaw member 22 is moveable about pivot pin 34 relative to shaft 14 and fixed jaw member 24.

The knife blade channels 53 on the jaw members 22, 24 are aligned with the knife blade assembly 50 to accommodate reciprocation of the knife blade 52 therethrough when a trigger 11 of the trigger assembly 10 is moved proximally (FIG. 8).

Knife blade assembly 50 is disposed within shaft 14 and is translatable therethrough from an initial retracted configuration to an extended configuration into the knife blade channels 53 on the jaw members 22, 24. Knife blade assembly 50 includes a generally elongated configuration having a split or bifurcated medial portion 55 including two legs 55*a* and 55*b* defining an opening 57 therebetween that is configured to receive the pivot pin 56 and cam pin 78 therethrough (FIGS. 4-8). The opening 57 is configured to permit translation of the knife blade assembly through the mechanism 40 while allowing the mechanism 40 to pivot about the pivot pin 56 and the cam pin 78 to translate within the elongated cam slot 68 when the trigger 11 is moved proximally.

A knife blade assembly return spring 36 (FIGS. 2, 5 and 7) is supported on the shaft 14. The knife blade assembly return spring 36 is utilized to return the knife blade assembly 50 including the knife blade 51 to the initial retracted configuration when the trigger 11 is released.

In use, drive tube 38 is, initially, in an extended configuration and the jaw members 22 and 24 are an open configuration to receive or position tissue therebetween (FIGS. 1-3). In this extended configuration of the drive tube 38, the cam pin 78 is positioned at the distal end 72 of the elongated cam slot 68 and the finger 64 of the mechanism 40 is engaged with the notched portion 62 of the knife blade assembly 50. When the finger 64 of the mechanism 40 is engaged with the notched portion 62, the knife blade assembly 50 including the knife blade 51 is prevented from moving. The unique configuration of the mechanism 40 overcomes aforementioned drawbacks discussed above that are typically associated with conventional forceps. In particular, the likelihood of the knife blade assembly 50 including the knife blade 51 inadvertently moving between the jaw members 22, 24, such as, for example, when large tissue is positioned therebetween, is greatly reduced, if not completely eliminated. In other words, this greatly reduces, if not completely eliminates "blade trap" from occurring.

In certain instances, when the mechanism 40 is engaged with the knife blade assembly 50, the mechanism 40 could be used to limit the travel of the knife blade assembly 50. In this instance, for example, the knife blade assembly 50 could deploy partially, but not beyond a "safe" distance where the knife blade assembly 50 is at risk of becoming trapped between the jaw members 22, 24. As can be appreciated, this may prevent a surgeon from becoming frustrated (or confused) that the knife blade assembly 50 cannot be deployed and would maintain partial functionality of the knife blade assembly 50 even on thick tissue.

To move the jaw members 22, 24 toward one another, the movable handle 28 is approximated toward the fixed handle 26. Approximation of the movable handle 28 causes the drive tube 38 to move proximally, which has a two-fold effect. One, the drive tube 38 moves the cam pin 44 (FIGS. 1 and 8) proximally, which, in turn, moves the jaw members 22, 24 toward one another and the clamping configuration. Two, the drive tube 38 moves the cam pin 78 proximally towards the proximal end 70 until such time that the cam pin 78 contacts the ramp portion 76, which, in turn, causes the mechanism 40 to pivot about the pivot pin 56, which, in turn, causes the finger portion 64 to disengage from the notched portion 62 of the knife blade assembly 50. With the finger portion 64 disengaged from the notched portion 62, the knife blade 51 of the knife blade assembly 50 is free to translate within a pair of knife blade channels 53 disposed on the jaw members 22, 24 of the end effector 12 (FIGS. 2-3 and 8).

With reference to FIGS. 9-14, a mechanism 140 according to an alternate embodiment of the present disclosure is illustrated that may be utilized with the forceps 2. Only those operative features that are unique to the functionality of the mechanism 140 are described herein.

Figure 9:
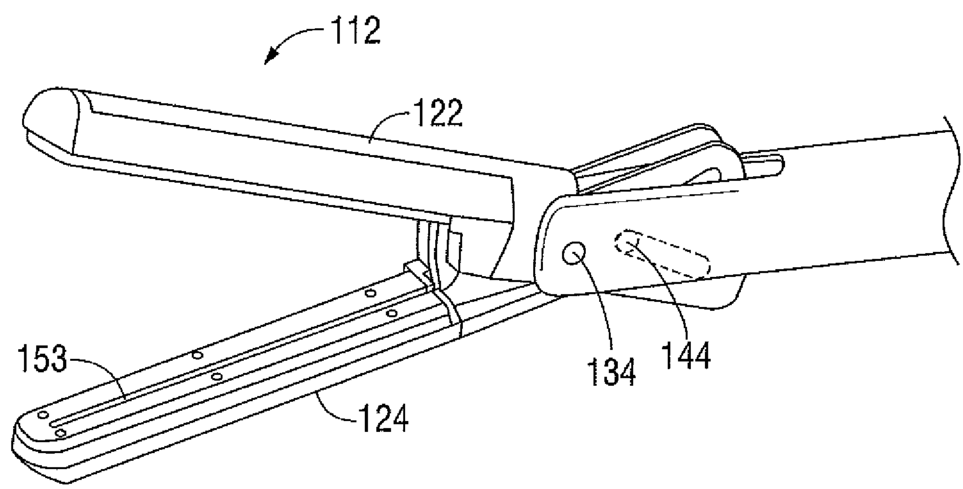
FIG. 9 is a perspective view of an end effector depicted in FIG. 1 with a knife blade lockout mechanism according to an alternate embodiment of the present disclosure.
Figure 10:
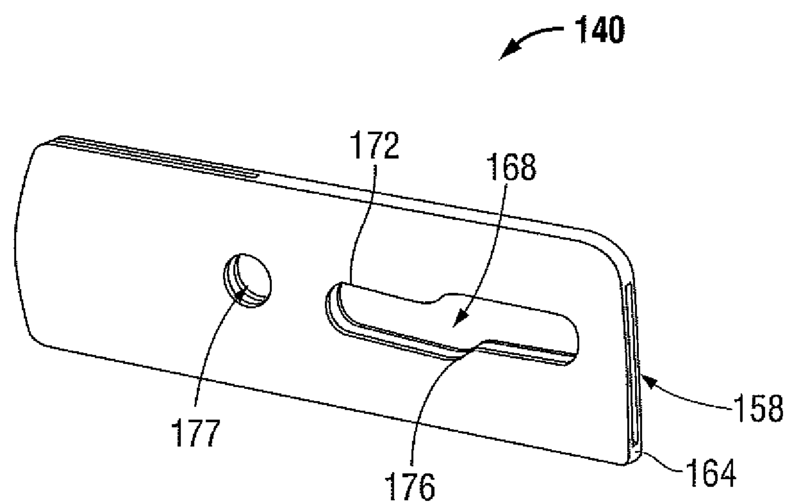
FIG. 10 is a perspective view of the knife blade lockout mechanism depicted in FIG. 9.
Figure 11:
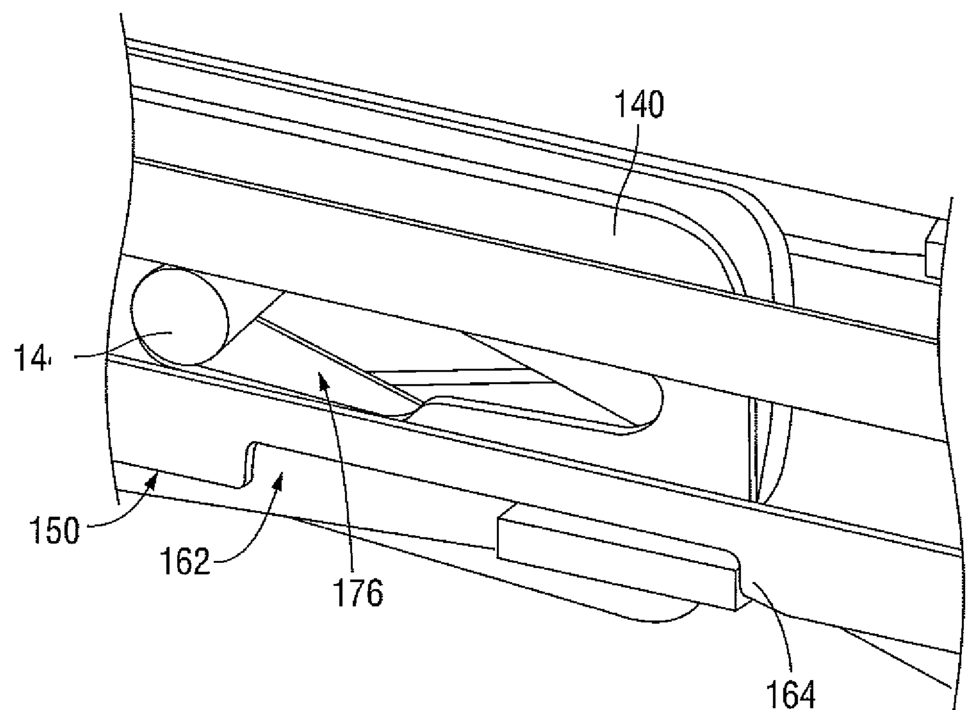
FIG. 11 is a perspective view of the knife blade lockout mechanism shown in an engaged configuration.
Figure 12:
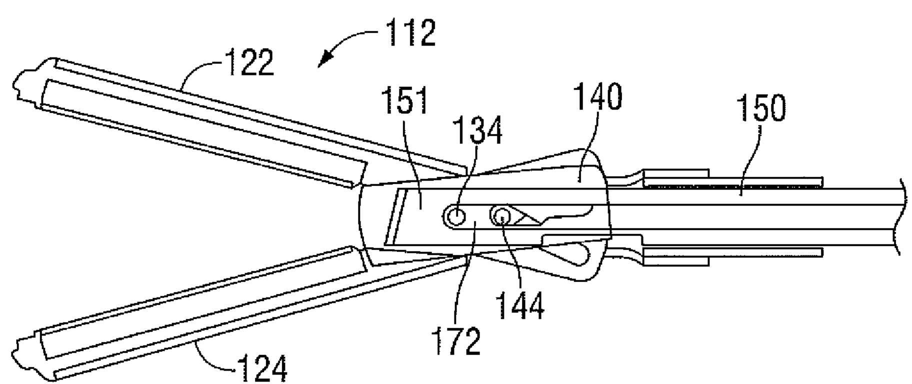
FIG. 12 is a side view of the end effector depicted in FIG. 9 with the knife blade lockout mechanism shown in the engaged configuration.
Figure 13:
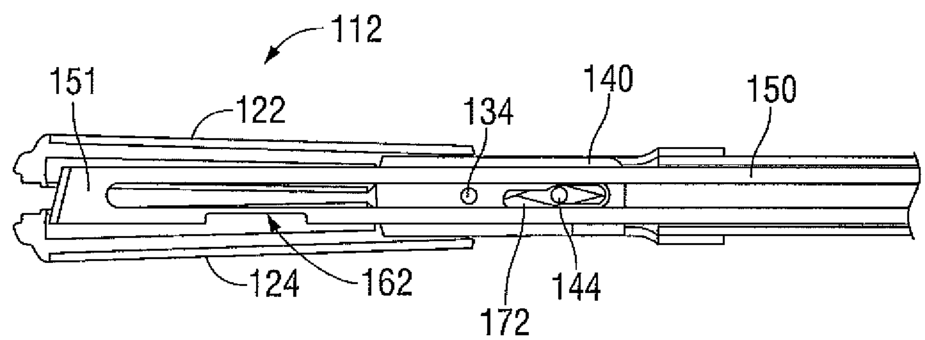
FIG. 13 is a side view of the end effector depicted in FIG. 9 with the knife blade lockout mechanism shown in a disengaged configuration.

Unlike mechanism 40 that is positioned proximal with respect to the jaw members 22, 24, mechanism 140 is positioned between the jaw members 122, 124 of the end effector 112 (FIGS. 9, 12 and 13). Moreover, unlike mechanism 40 that utilized its own pivot pin 56 and cam pin 78, mechanism 140 is operably coupled to the pivot pin 134 and cam pin 144 that are configured to function in a manner described above (FIG. 9). Further, in the embodiment illustrated in FIGS. 9-14, the elongated cam slot 168 is disposed proximal with respect to the aperture 177, i.e., pivot pin 134 is disposed distal with respect to cam pin 144 (FIG. 10). Finger 64 is replaced by a bottom wall 164 (FIG. 10) that is configured to engage the notched portion 162 of the knife blade assembly 150. Bottom wall 164 is positioned at the open trailing end 158 as opposed to the finger 64 that is positioned at the open leading end 60.

In use, the drive tube 38 is, initially, in an extended configuration and the jaw members 122 and 124 are in an open configuration to receive or position tissue therebetween (FIGS. 9-10 and 12). In this extended configuration of the drive tube 38, the cam pin 144 is positioned at the distal end 172 of the elongated cam slot 168 and the bottom wall 164 of the mechanism 140 is engaged with the notched portion 162 (FIG. 11) of the knife blade assembly 150. When the bottom wall 164 of the mechanism 140 is engaged with the notched portion 162, the knife blade assembly 150 including the knife blade 151 is prevented from moving (FIG. 12). The above described advantages are also achieved with the mechanism 140 when compared to conventional forceps.

To move the jaw members 122, 124 toward one another, the movable handle 28 is approximated toward the fixed handle 26. Approximation of the movable handle 28 causes the drive tube 38 to move proximally, which has a two-fold effect. One, the drive tube 38 moves the cam pin 144 proximally, which, in turn, moves the jaw members 122, 124 toward one another and to the clamping configuration. Two, the drive tube 38 moves the cam pin 144 proximally towards the proximal end 170 until such time that the cam pin 144 contacts the ramp portion 176 (FIG. 11), which, in turn, causes the mechanism 140 to pivot about the pivot pin 134, which, in turn, causes the bottom wall 164 to disengage from the notched portion 162 of the knife blade assembly 150. With the bottom wall 164 disengaged from the notched portion 162, the knife blade 151 of the knife blade assembly 150 is free to translate within the pair of knife blade channels 153 (FIG. 9) disposed in the jaw members 122, 124 of the end effector 112 (FIG. 13).

With reference to FIGS. 14-17, a mechanism 240 according to another alternate embodiment of the present disclosure is illustrated that may be utilized with the forceps 2. Only those operative features that are unique to the functionality of the mechanism 240 are described herein.

Figure 16:
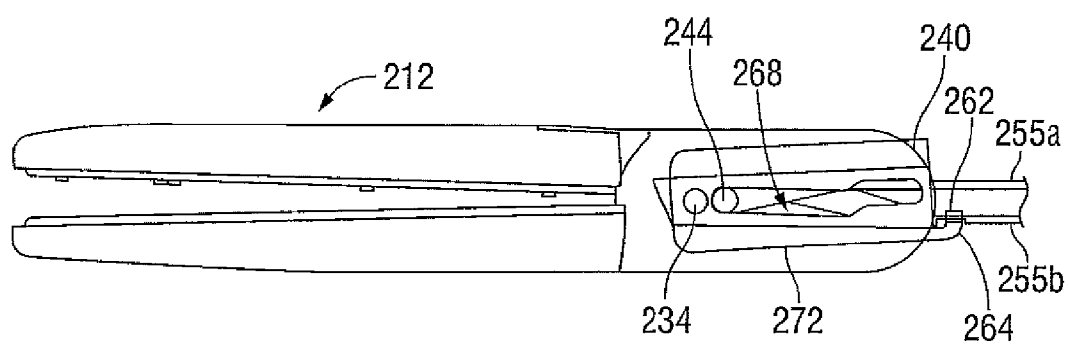
FIG. 16 is a side view of the end effector depicted in FIG. 14 with the knife blade lockout mechanism shown in the engaged configuration.

Unlike mechanism 140, mechanism 240 includes a protrusion 264 (FIG. 15) that is configured to engage the notch 262 to prevent the knife blade assembly 250 from moving (FIG. 16). Protrusion 264 includes a generally arcuate configuration and is positioned at the open trailing end 260. A slit 265 is provided at a top surface of the protrusion 264 and is configured to releasably engage a portion of the notched portion 262 (e.g., adjacent the bifurcated leg 255*b*) such that a press-fit, friction-fit, etc. is created therebetween. As can be appreciated, this press or friction-fit facilitates maintaining the protrusion 264 and notched portion 262 in substantial alignment with one another.

In use, the drive tube 38 is, initially, in an extended configuration and the jaw members 222 and 224 are an open configuration to position tissue therebetween (FIG. 16). In this extended configuration of the drive tube 38, the cam pin 244 is positioned at the distal end 272 of the elongated cam slot 268 and the protrusion 264 of the mechanism 240 is engaged with the notched portion 262 of the knife blade assembly 250 (FIG. 16). When the protrusion 264 of the mechanism 240 is engaged with the notched portion 262, the knife blade assembly 250 (FIG. 14) including the knife blade 251 (FIGS. 16-17) is prevented from moving. The above described advantages are also achieved with the mechanism 140 when compared to conventional forceps.

Figure 14:
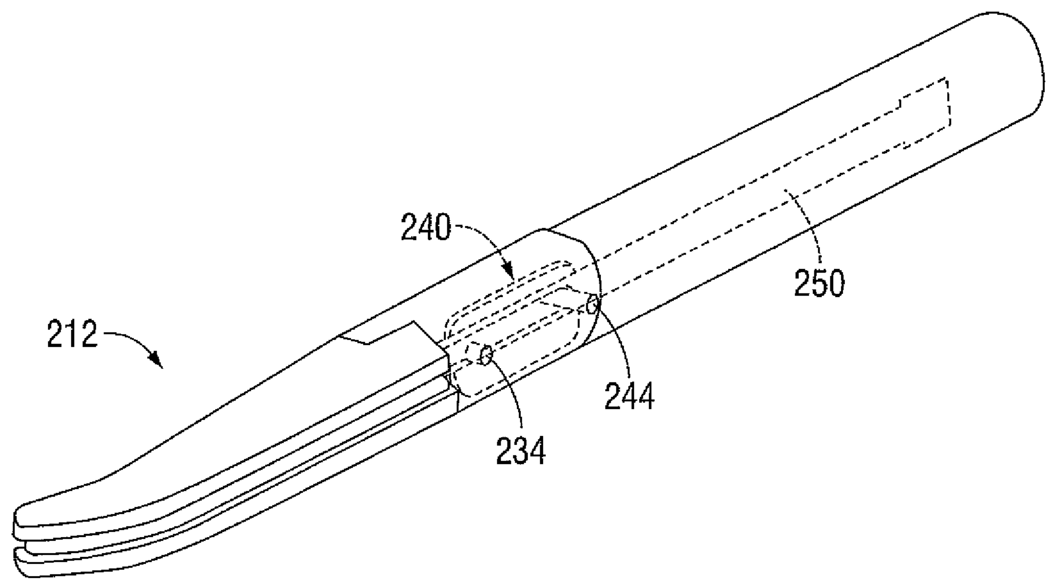
FIG. 14 is a perspective view of an end effector with a knife blade lockout mechanism according to another embodiment of the present disclosure.
Figure 15:
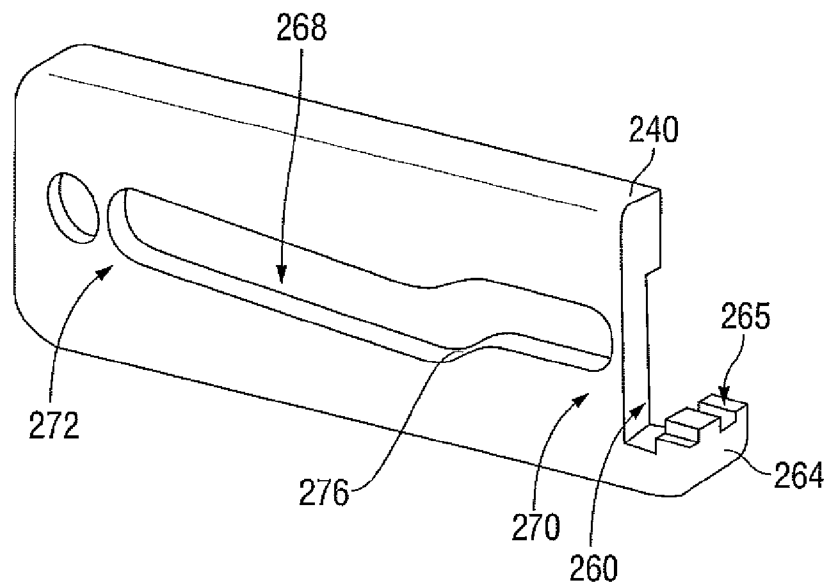
FIG. 15 is a perspective view of the knife blade lockout mechanism depicted in FIG. 14.
Figure 17:
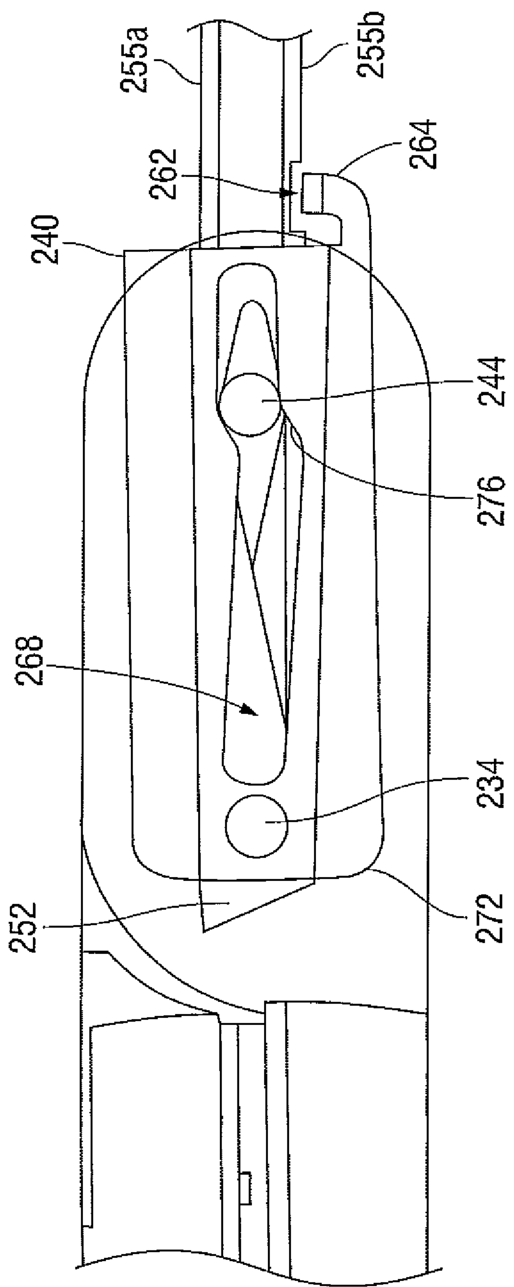
FIG. 17 is a partial, side view of the end effector depicted in FIG. 14 with the knife blade lockout mechanism shown in a disengaged configuration.

To move the jaw members 222, 224 toward one another, the movable handle 28 is approximated toward the fixed handle 26. Approximation of the movable handle 28 causes the drive tube 38 to move proximally, which has a two-fold effect. One, the drive tube 38 moves the cam pin 244 proximally, which, in turn, moves the jaw members 222, 224 toward one another and the clamping configuration. Two, the drive tube 38 moves the cam pin 244 proximally towards the proximal end 270 until such time that the cam pin 244 contacts the ramp portion 276 (FIG. 16), which, in turn, causes the mechanism 240 to pivot about the pivot pin 234, which, in turn, causes the protrusion 264 to disengage from the notched portion 262 of the knife blade assembly 250 (FIG. 17). With the protrusion 264 disengaged from the notched portion 262, the knife blade 251 of the knife blade assembly 250 is free to translate within the pair of knife blade channels (not explicitly shown) disposed in the jaw members 222, 224 of the end effector 212 (FIG. 14).

From the foregoing and with reference to the various figure drawings, those skilled in the art will appreciate that certain modifications can also be made to the present disclosure without departing from the scope of the same. For example, in certain instances one or more resilient members, such as, for example, a spring or the like may be operably coupled to any of the aforementioned mechanisms 40, 140, 240 to facilitate pivoting thereof about the respective pivot pins 56, 134, 234.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:

a housing having a shaft extending therefrom;

an end effector assembly operably coupled to a distal end of the shaft and including a pair of first and second jaw members, at least one of the first and second jaw members movable from an open configuration for positioning tissue therebetween, to a clamping configuration for grasping tissue therebetween;

a knife blade assembly including a knife blade translatable within the first and second jaw members when the first and second jaw members are in the clamping configuration; and a knife blade lockout mechanism supported within the shaft and in operative communication with the knife blade assembly, the knife blade lockout mechanism including an elongated cam slot with a cam pin translatable therein from a distal end of the elongated cam slot corresponding to the first and second jaw members being in the open configuration and the knife blade lockout mechanism engaged with the knife blade assembly, to a proximal end of the elongated cam slot corresponding to the first and second jaw members being in the clamping configuration and the knife blade lockout mechanism disengaged from the knife blade assembly.

2. An electrosurgical forceps according to claim 1, wherein, when the knife blade lockout mechanism is engaged with the knife blade assembly, the knife blade is prevented from translating within the first and second jaw members, and when the knife blade lockout mechanism is disengaged from the knife blade assembly the knife blade is capable of translating within the first and second jaw members.

3. An electrosurgical forceps according to claim 1, wherein the knife blade lockout mechanism includes a generally rectangular configuration having open leading and trailing ends.

4. An electrosurgical forceps according to claim 3, wherein the open leading end is configured to selectively engage a notched portion of the knife blade assembly.

5. An electrosurgical forceps according to claim 3, wherein a protrusion is disposed adjacent the open trailing end of the knife blade lockout mechanism and is configured to selectively engage a notched portion of the knife blade assembly.

6. An electrosurgical forceps according to claim 1, wherein the knife blade lockout mechanism is operably positioned between the first and second jaw members.

7. An electrosurgical forceps according to claim 6, wherein the first and second jaw members are pivotably coupled to one another via a pivot pin extending through the knife lockout mechanism and the shaft, and wherein the cam pin disposed within the elongated cam slot is disposed within respective cam slots of the first and second jaw members and operably coupled to a drive tube of the electrosurgical forceps to move the first and second jaw members from the open configuration to the clamping configuration.

8. An electrosurgical forceps according to claim 7, wherein the knife blade lockout mechanism is pivotable about the pivot pin to provide selective engagement between the knife blade lockout mechanism and the knife blade assembly.

9. An The electrosurgical forceps according to claim 1, wherein the knife blade lockout mechanism is positioned proximal to the first and second jaw members.

10. An electrosurgical forceps according to claim 9, wherein the first and second jaw members are pivotably coupled to one another via a pivot pin extending through the shaft, and wherein the cam pin disposed within the elongated cam slot of the knife blade lockout mechanism is disposed within respective cam slots of the first and second jaw members and is operably coupled to a drive tube of the electrosurgical forceps to move the first and second jaw members from the open configuration to the clamping configuration.

11. An electrosurgical forceps according to claim 9, wherein the first and second jaw members are pivotably coupled to one another via a first pivot pin extending through the shaft, wherein a second pivot pin extending through the knife blade lockout mechanism is positioned within a pair of slots defined through the drive tube such that the knife blade lockout mechanism pivots about the second pivot pin when the drive tube is actuated.

12. An electrosurgical forceps according to claim 11, wherein distal ends of the pair of slots defined in the drive tube function as a hard stop for the first and second jaw members to provide a predetermined gap distance between the first and second jaw members when the first and second jaw members are in the clamping configuration.

13. An electrosurgical forceps according to claim 1, further comprising a knife blade assembly return spring that is configured to return the knife blade assembly to an initial retracted position.

14. The electrosurgical forceps according to claim 1, wherein the knife blade lockout mechanism includes a ramp that separates the proximal and distal ends of the elongated cam slot, the knife blade lockout mechanism preventing the knife blade from translating within the first and second jaw members while the cam pin is positioned within the distal end of the elongated cam slot, the knife blade translatable within the first and second jaw members while the cam pin is positioned within the proximal end of the elongated cam slot.

15. An electrosurgical forceps, comprising:

a housing having a shaft extending therefrom;

an end effector assembly operably coupled to a distal end of the shaft and including a pair of first and second jaw members, at least one of the first and second jaw members movable from an open configuration for positioning tissue therebetween, to a clamping configuration for grasping tissue therebetween;

a knife blade assembly including a knife blade translatable within the first and second jaw members when the first and second jaw members are in the clamping configuration; and a knife blade lockout mechanism supported within the shaft and configured to allow passage of the knife blade assembly therethrough for selective engagement with the knife blade assembly to lock the knife blade in an initial retracted position, the knife blade lockout mechanism includes a generally rectangular configuration having open leading and trailing ends at least one of which configured to selectively engage a notched portion of the knife blade assembly, the knife blade lockout mechanism including an elongated cam slot with a cam pin translatable therein from a distal end of the elongated cam slot corresponding to the first and second jaw members being in the open configuration and the knife blade lockout mechanism engaged with the knife blade assembly, to a proximal end of the elongated slot corresponding to the first and second jaw members being in the clamping configuration and the knife blade lockout mechanism disengaged from the knife blade assembly.

16. An electrosurgical forceps according to claim 15, wherein the knife blade lockout mechanism is operably positioned between the first and second jaw members.

17. An electrosurgical forceps according to claim 16, wherein the first and second jaw members are pivotably coupled to one another via a pivot pin extending through the knife blade lockout mechanism and the shaft, and wherein the cam pin disposed within the elongated cam slot is disposed within respective cam slots of the first and second jaw members and operably coupled to a drive tube of the electrosurgical forceps to move the first and second jaw members from the open configuration to the clamping configuration, wherein the knife blade lockout mechanism is pivotable about the pivot pin to provide selective engagement between the knife blade lockout mechanism and the knife blade assembly.

18. An electrosurgical forceps according to claim 15, wherein the knife blade lockout mechanism is positioned proximal to the first and second jaw members, wherein the first and second jaw members are pivotably coupled to one another via a pivot pin extending through the shaft, and wherein the cam pin disposed within the elongated cam slot of the knife blade lockout mechanism is disposed within respective cam slots of the first and second jaw members and operably coupled to a drive tube of the electrosurgical forceps to move the first and second jaw members from the open configuration to the clamping configuration.

19. An electrosurgical forceps according to claim 15, wherein the knife blade lockout mechanism is positioned proximal to the first and second jaw members, wherein the first and second jaw members are pivotably coupled to one another via a first pivot pin extending through the shaft, wherein a second pivot pin extending through the knife blade lockout mechanism is positioned within a pair of slots defined through the drive tube such that the knife blade lockout mechanism pivots about the second pivot pin when the drive tube is actuated, wherein a distal end of the slot in the drive tube functions as a hard stop for the first and second jaw members to provide a predetermined gap distance between the first and second jaw members when the first and second jaw members are in the clamping configuration.

20. An electrosurgical forceps according to claim 15, further comprising a knife blade assembly return spring that is configured to return the knife blade assembly to its initial retracted position.

* * * * *